US00PP20557P2

(12) United States Plant Patent
Pan

(10) Patent No.: US PP20,557 P2
(45) Date of Patent: Dec. 15, 2009

(54) ***LANTANA* PLANT NAMED 'BANT TRAGOL'**

(50) Latin Name: *Lantana camara L.*
Varietal Denomination: Bant Tragol

(75) Inventor: Shifeng Pan, Hollister, CA (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 12/291,202

(22) Filed: Nov. 7, 2008

(51) Int. Cl.
*A01H 5/00* (2006.01)

(52) U.S. Cl. ..... Plt./227

(58) Field of Classification Search ..... Plt./227
See application file for complete search history.

*Primary Examiner*—Annette H Para
(74) *Attorney, Agent, or Firm*—S. Matthew Edwards

(57) ABSTRACT

A new *Lantana* plant named 'Bant Targol,' particularly distinguished by yellow/orange flower color, medium size flowers, good floriferiousness, sets very few seeds, a flat trailing habit that is well branched, and has dark green foliage.

1 Drawing Sheet

Latin name of the genus and species of the plant claimed: *Lantana camara L.*

Varietal denomination: 'Bant Tragol'.

BACKGROUND OF THE NEW PLANT

The present invention comprises a new *Lantana,* botanically known as *Lantana camara L.* and hereinafter referred to by the variety name 'Bant Tragol.'

'Bant Tragol' is a product of a planned breeding program. The new cultivar 'Bant Tragol' has yellow/orange flower color, medium size flowers, good floriferiousness, sets very few seeds, a flat trailing habit that is well branched, and has dark green foliage.

'Bant Tragol' originated from a selfing of a female hybrid in a controlled breeding program in Gilroy, Calif. The female parent was an unpatented hybrid seedling identified as '9-2' with gold color. '9-2' has less vigor, a taller plant habit and is later to flower than 'Bant Tragol.'

'Bant Tragol' was selected as one flowering plant within the progeny of the stated cross in May 2005 in a controlled environment in Gilroy, Calif. The pollination took place in July 2004 and the seed sowing in November 2004.

The first act of asexual reproduction of 'Bant Tragol' was accomplished when vegetative cuttings were taken from the initial selection in the May 2005 in a controlled environment in Gilroy, Calif.

Horticultural examination of plants grown from cuttings of the plant initiated in May 2005 in Gilroy, Calif., and continuing thereafter, has demonstrated that the combination of characteristics as herein disclosed for 'Bant Tragol' are firmly fixed and are retained through successive generations of asexual reproduction.

'Bant Tragol' has not been observed under all possible environmental conditions. The phenotype may vary significantly with variations in environment such as temperature, light intensity and day length.

A Plant Breeder's Right for this cultivar was applied for in Canada on Dec. 24, 2007. 'Bant Tragol' has not been made publicly available more than one year prior to the filing of this application.

DESCRIPTION OF THE DRAWINGS

The accompanying photographic drawing shows typical flower and foliage characteristics of 'Bant Tragol' with colors being as true as possible with an illustration of this type. The photographic drawing shows three flowering potted plants of the new variety in a 14 inch container, grown and photographed August 2007 in Colorado, USA. These plants were approximately 6 months old. The close-up photograph was grown and photographed in May 2008 in Gilroy, Calif. This plant was approximately 3–4 months old.

DETAILED BOTANICAL DESCRIPTION

The measurements were taken in Gilroy, Calif., in April 2008 on plants that were growing in 4 inch pots in a trial setting. Culture of these plants started in January 2008 in a greenhouse. The plants were approximately 4 months old.

Color Chart used: Royal Horticultural Society Colour Chart (R.H.S.) 2001

BRIEF SUMMARY OF INVENTION

The following observations, measurements, and comparisons describe plants grown outside in Gilroy, Calif. The following traits have been repeatedly observed and are determined to be basic characteristics of the new variety. The combination of these characteristics distinguishes this *Lantana* as a new and distinct variety.

TABLE 1

DIFFERENCES BETWEEN THE NEW VARIETY 'BANT TRAGOL' AND A SIMILAR VARIETY

| | 'Bant Tragol' | 'New Gold' (Not patented) |
|---|---|---|
| Flower color | Slightly deeper yellow/orange | Lighter yellow/orange |
| Flower size | Larger flowers | Smaller flowers |
| Plant habit | Tighter/spreading habit | More open habit |

Plant:

*Form, growth and habit.*—Flat, trailing habit that is well branched, apical pinching enhances the number of branches and results in a tighter plant habit.

*Plant height.*—10–15 cm.

*Plant height* (*inflorescence included*).—14–18 cm.

*Plant width.*—45–60 cm.

Foliage:

*Type.*—Opposite.

*Immature, leaf color, upper surface.*—RHS 147A.

*Lower surface.*—RHS 147B.

*Mature, leaf color, upper surface.*—RHS 147A, but a little darker.

*Lower surface.*—RHS 147B.

*Length.*—3.9–4.2 cm.

*Width.*—2.3–2.7 cm.

*Shape.*—Ovate.

*Base shape.*—Attenuate.

*Apex shape.*—Acute.

*Margin.*—Serrate.

*Texture, upper surface.*—Hirsute; glandular hairs.

*Texture, lower surface.*—Hirsute, mainly on the veins; glandular hairs.

*Color of veins, upper surface.*—Both surfaces; RHS 144A basally, otherwise indistinct.

*Petioles color.*—RHS N144A.

*Petioles length.*—0.4–0.6 cm.

*Diameter of petiole.*—0.1–0.15 cm.

*Texture.*—Both surfaces, hirsute.

Stem:

*Color of stem.*—Upper side RHS 166A but a little more purple, lower side RHS 144A.

*Length of stem.*—35–40 cm.

*Diameter.*—0.3–0.4 cm.

*Length of internodes.*—1.5–3.5 cm.

*Texture.*—Slightly hispid; glandular hairs.

Inflorescence:

*Type.*—Umbel like; flattened semi-sphere, the florets are sessile on an ovate receptacle.

*Blooming habit.*—Flowers continuously from spring through fall.

*Number of open flowers per inflorescence.*—25–30.

*Quantity of inflorescences per plant.*—About 100, including those with only buds.

*Lastingness of individual blooms on the plant.*—About 4 weeks depending on temperatures.

*Fragrance.*—Slightly spicy.

*Umbel horizontal diameter.*—3.4–3.7 cm.

*Umbel vertical height.*—1.8–2.3 cm.

*Peduncle color.*—RHS 144B with a hint of anthocyanins of about RHS 183D on the lower side.

*Length of peduncle.*—3–4 cm.

*Peduncle diameter.*—0.15 cm.

*Texture.*—Slightly hispid; glandular hairs.

Corolla:

*Floret form.*—Salver-shaped to shallow cup-shaped and zygomorphic, with a relatively long tube at the base. Each flower subtended by a single bract.

*Length of floret.*—1.5–1.6 cm.

*Width of floret.*—0.9–1.0 cm.

*Immature, color of petals, upper surface.*—Closest to RHS 17C.

*Lower surface.*—RHS 13A.

*Mature, color of petals, upper surface.*—RHS 21A.

*Lower surface.*—RHS 21C.

*Petal length.*—0.4–0.5 cm.

*Petal diameter.*—0.3–0.6 cm.

*Apex.*—Mucronulate.

*Margin.*—Entire.

*Shape.*—Obovate.

*Degree of lobation.*—Moderate.

*Texture, upper surface.*—Papillose.

*Texture, lower surface.*—Slightly hirsute basally.

*Corolla tube, color, outer surface.*—Between RHS 21B and C.

*Corolla tube, color, inner surface.*—RHS 21C.

*Corolla tube length.*—1.0–1.1 cm.

*Diameter* (*at opening*).—1.0 cm.

*Corolla tube texture, outer surface.*—Hirsute.

*Corolla tube texture, inner surface.*—Glabrous, hirsute towards apex.

Bud (just before opening):

*Color.*—RHS 15A.

*Length.*—0.3–0.4 cm.

*Width.*—0.3 cm at the tip.

*Shape.*—Tubular.

Bract:

*Color.*—RHS 146C.

*Length.*—0.3–0.4 cm.

*Diameter.*—0.15–0.2 cm.

*Texture, upper surface.*—Glandular hairs.

*Texture, lower surface.*—Hirsute at apex.

Calyx:

*Number of sepals.*—5, fused sepals forming a short tube around the base of each floret.

*Color of sepals.*—RHS 144B.

*Length of sepals.*—0.2–0.3 cm.

*Width of sepals.*—0.2 cm.

*Apex shape.*—Obtuse.

*Apex margins.*—Shallowly fringed.

*Texture, upper surface.*—Slightly hirsute.

*Texture, lower surface.*—Glabrous.

Reproductive organs:

*Pistil.*—1.

*Length.*—0.3 cm.

*Style color.*—RHS 4D.

*Style length.*—0.2 cm.

*Stigma color.*—RHS N144A.

*Stamens.*—4.

*Color of filaments.*—RHS 20C.

*Length of filaments.*—0.5 cm.

*Anther color.*—RHS 199C.

*Length of anthers.*—0.1 cm.

*Pollen amount.*—Sparse.

*Color of pollen.*—RHS 13C.

*Fertility/seed set.*—This hybrid sets very few seeds and those seeds were not observed for characteristics.

Disease/pest resistance: Disease resistance or susceptibility has not been observed on this hybrid.

What is claimed is:

1. A new and distinct variety of *Lantana* plant named 'Bant Targol,' substantially as illustrated and described herein.

* * * * *

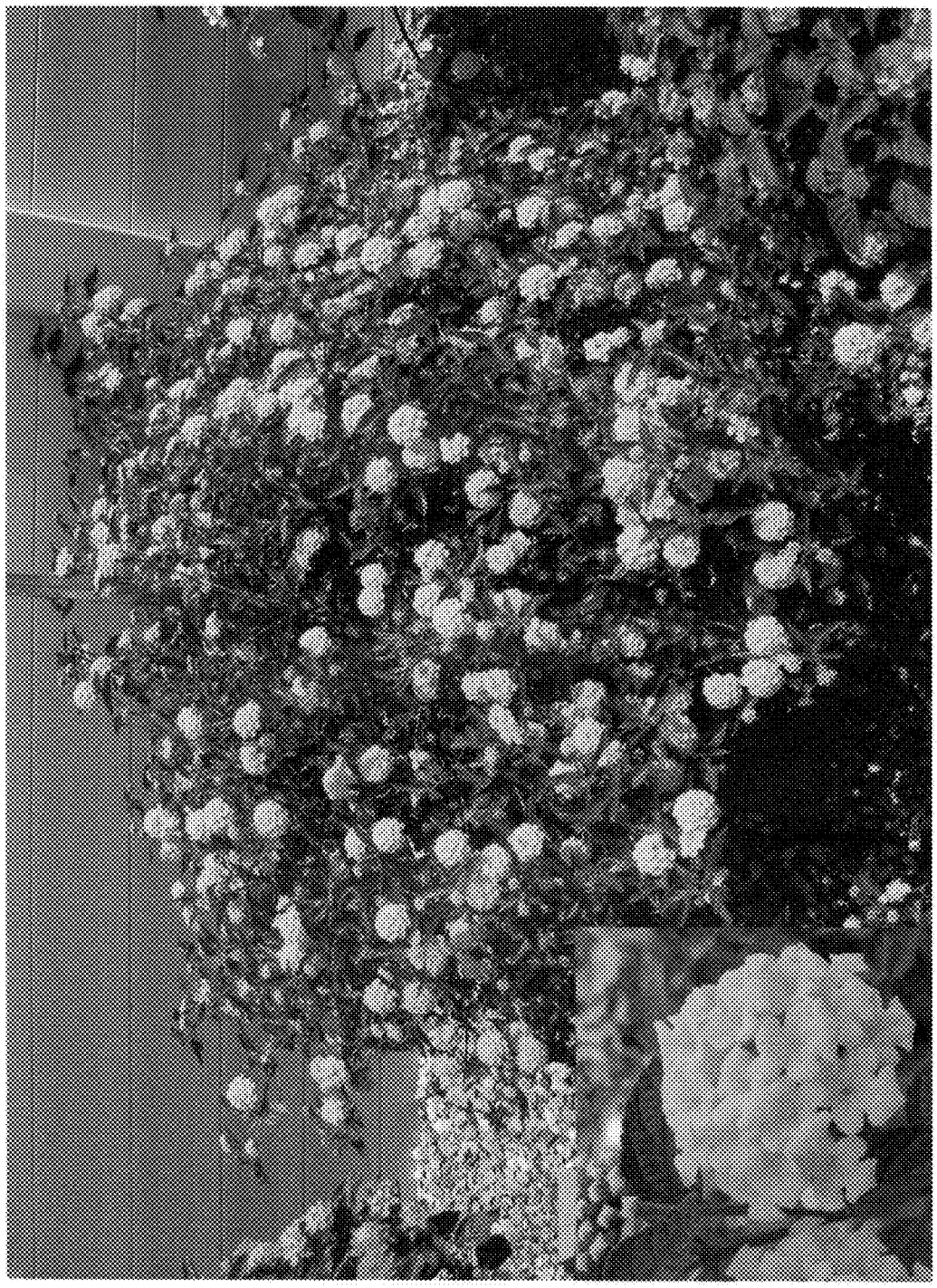

UNITED STATES PATENT AND TRADEMARK OFFICE

CERTIFICATE OF CORRECTION

PATENT NO. : PP 20,557 P2
APPLICATION NO. : 12/291202
DATED : December 15, 2009
INVENTOR(S) : Pan It is certified that error appears in the above-identified patent and that said Letters Patent is hereby corrected as shown below:

Title page, item [57] line 1 ABSTRACT, delete "Targol," and insert therefor --Tragol,--

At column 4, in claim 1, delete "Targol," and insert therefor --Tragol,--

Signed and Sealed this

Second Day of February, 2010

David J. Kappos

David J. Kappos
*Director of the United States Patent and Trademark Office*